US008222275B2

(12) United States Patent
Baraldi et al.

(10) Patent No.: US 8,222,275 B2
(45) Date of Patent: Jul. 17, 2012

(54) BIARYLCARBOXYARYLAMIDES AS VANILLOID-1 RECEPTOR MODULATORS

(75) Inventors: Pier Giovanni Baraldi, Ferrara (IT);
Pier Andrea Borea, Ferrara (IT);
Pierangelo Geppetti, Ferrara (IT);
Maria Giovanna Pavani, Ferrara (IT);
Francesca Fruttarolo, Ferrara (IT);
Marcello Trevisani, Ferrara (IT)

(73) Assignee: Pharmeste S.R.L., Ferrara (IT)

( * ) Notice: Subject to any disclaimer, the term of this patent is extended or adjusted under 35 U.S.C. 154(b) by 600 days.

(21) Appl. No.: 12/307,921

(22) PCT Filed: Jul. 2, 2007

(86) PCT No.: PCT/EP2007/005835
§ 371 (c)(1),
(2), (4) Date: Jul. 9, 2009

(87) PCT Pub. No.: WO2008/006480
PCT Pub. Date: Jan. 17, 2008

(65) Prior Publication Data
US 2010/0081687 A1      Apr. 1, 2010

(30) Foreign Application Priority Data

Jul. 10, 2006   (EP) .................................... 06014302

(51) Int. Cl.
*C07D 401/04*       (2006.01)
*A61K 31/47*        (2006.01)

(52) U.S. Cl. ....................................... 514/307; 546/146
(58) Field of Classification Search .......................... None
See application file for complete search history.

(56) References Cited

U.S. PATENT DOCUMENTS 7,919,624 B2   4/2011 Baraldi et al.

FOREIGN PATENT DOCUMENTS

| WO | 03/024920 | 3/2003 |
|---|---|---|
| WO | 03/049702 | 6/2003 |
| WO | 2004/056774 | 7/2004 |

OTHER PUBLICATIONS

PCT International Search Report for PCT/EP2007/005844 filed on Jul. 2, 2007 in the name of Pharmeste S.R.L.
PCT Written Opinion for PCT/EP2007/005844 filed on Jul. 2, 2007 in the name of Pharmeste S.R.L.
PCT International Preliminary Report on Patentability for PCT/EP2007/005844 filed on Jul. 2, 2007 in the name of Pharmeste S.R.L.
Giovanni Appendino et al., "Clinically Useful Vanilloid Receptor RPVI Antagonists: Just around the Corner (or too Early to Tell)?", Progress in Medicinal Chemistry 2006, 44, 145-180.
Timor Baasov et al., "C-C Stretching Frequencies in Model Compounds of the Protonated Retinal Schiff Base", Angew. Chem. 1984, 23, 803-804.
P.G. Baraldi et al., "A Facile, Efficient of 2-substituted-4-Hydroxy-2-cyclopenten-1-ones", S. Synthesis 1986, 9, pp. 781-782.
Doherty, Elizabeth M et al., "Discovery of potent, orally available vanilloid receptor-1 antagonists. Structure-activity relationship of N-aryl cinnamides," Journal of Medicinal Chemistry, vol. 48, No. 1, pp. 71-90, Jan. 13, 2005.
Gunthorpe M J et al., "Identification and characterization of SB-366791, a potent and selective vanilloid receptor (VR1/TRPV1) antagonist,"Neuropharmacology, Pergamon Press, Oxford, GB, vol. 46, No. 1, pp. 133-149, Jan. 2004.
Yoshihisa Kudo et al., "Monitoring of Intracellular Ca2+ Elevation in a Single Neural Cell Using a Fluorescence Microscope/Video-Camera System", Japan. J. Pharmacol. 41. 345-351 (1986).
Peter Meier et al, "Synthesis of Fonnylphenylpyridinecarboxylic Acids Using Suzuki-Miyaura Coupling Reactions", Synthesis 2003, 4, pp. 551-554.
Peter J. Munson et al., "Ligand: A Versatile Computerized Approach for Characterization of Ligand-Binding Systems", Analytical Biochemistry 107, 220-239 (1980).
M. Nanasawa et al., "The Favorskii-type Rearrangement of 3-Bromo-b-ionone with Sodium Ethoxide", Bull. Chem. Soc. Jpn. 1982, 55, 3655-3656.
Michela Rigoni et al., "Neurogenic responses mediated by vanilloid receptor-I (TRPVI) are blocked by the high affinity antagonist, iodo-resiniferatoxin", British Journal of Pharmacology (2003) 138, 977-985.
Wen-Chung Shieh et al., "A Simple Asymmetric Synthesis of 4-Arylphenylalanines via Palladium-Catalyzed Cross-Coupling Reaction of Arylboronic Acids with Tyrosine Triflate", J. Org. Chern. 1992, 57, 379-381.
Shimasake H et al., "Retinoidal dienamides and related aromatic amides. Replacement of the 9-ene structure of retinoic acid with a trans- or cis-amide group," Chemical and Pharmaceutical Bulletin, Japan, vol. 43, No. 1, pp. 100-107, 1995.
Arpad Szallasi et al., "[3H] resiniferatoxin binding by the vanilloid receptor: species-related differences, effects of temperature and sulfhydryl reagents", Naunyn-Schmiedeberg's Arch Pharmacol (1993) 347:84-91.
Arpad Szallasi et al., "Resiniferatoxin", M. Neurosciences 1992, 8, 368.
Jidong Zhang et al., "A colored dendrimer as a new soluble support in organic synthesis. Part 1: Suzuki reaction", Tetrahedron Letters 42 (2001) 6683-6686.

(Continued)

*Primary Examiner* — Zinna Northington Davis
(74) *Attorney, Agent, or Firm* — Steinfl & Bruno LLP

(57) ABSTRACT

The present invention provides compounds of formula (I): wherein A and Z are as defined in the description, along with methods for preparing such derivatives and their use for the treatment of inflammatory diseases such as neuropathic pain.

(I)

27 Claims, No Drawings

OTHER PUBLICATIONS

PCT International Search Report for PCT/EP2007/005835 filed on Jul. 2, 2007 in the name of Pharmeste S.R.L.

PCT Written Opinion for PCT/EP2007/005835 filed on Jul. 2, 2007 in the name of Pharmeste S.R.L.

Notice of Allowance issued for U.S. Appl. No. 12/307,919, filed Sep. 16, 2009 in the name of Baraldi et al. mail date: Jan. 6, 2011.

Medicament meaning and definition, Dictionary—eLook.org, retrieved from http://web.archive.org/web/20050521010727/http://www.elook.org/dicti, Jan. 17, 2012.

BIARYLCARBOXYARYLAMIDES AS VANILLOID-1 RECEPTOR MODULATORS

CROSS REFERENCE TO RELATED APPLICATIONS

This application is the national phase of International Application PCT/EP2007/005835 filed on Jul. 2, 2007 which, in turn, claims priority to European Patent Application 06014302.1 filed on Jul. 10, 2006.

FIELD OF THE INVENTION

The present invention relates to modulators of the vanilloid receptor, in particular to TRPV1 antagonists.

STATE OF THE ART

The Transient Receptor Potential Vanilloid 1 (TRPV1) is strongly involved in the genesis of thermal and mechanical hyperalgesia and has been proposed to play a key role in different pathological conditions including neuropathic pain and urological disorders.

Vanilloid receptor antagonists containing a biaryl moiety are known; WO 2004/056774[1] discloses, among others, the following substituted biaryl-4-carboxylic acid arylamides:

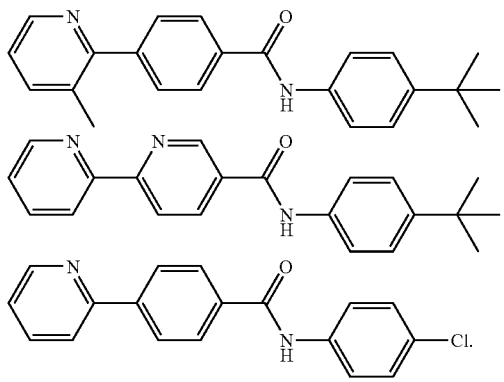

DESCRIPTION OF THE INVENTION

It has now been found that by replacing the pyridyl moiety in the above compounds with a isoquinolin-5-yl ring, TRPV1 antagonists with improved properties can be obtained Accordingly, the invention provides improved vanilloid-1 receptor modulators of general formula (I)

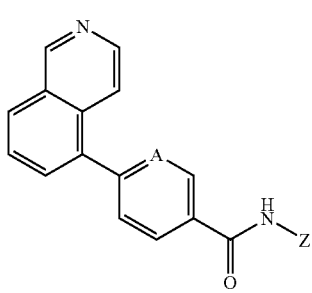

(I)

wherein:
A is CH or N;
Z is a phenyl or a pyridyl ring, optionally substituted with one or two R groups, which can be the same or different from one another and are selected from $C_1$-$C_4$ alkyl, preferably methyl, isopropyl or tert-butyl, $C_1$-$C_4$ haloalkyl, preferably trifluromethyl, or halogen.

For the purposes of the present description, halogen means a halogen atom selected from fluorine, chlorine, bromine and iodine, preferably chlorine.

A first group of preferred compounds of the invention is that of formula (Ia)

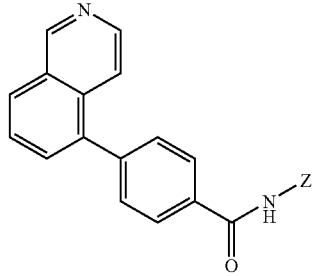

(Ia)

in which Z is as defined above.

A second group of preferred compounds according to the invention is that of formula (Ib)

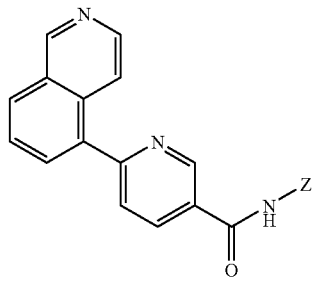

(Ib)

in which Z is as defined above.

In the compounds of formula (Ia) and (Ib) Z is preferably a phenyl ring substituted at the para-position with an R group other than hydrogen, preferably chlorine. The most preferred compound according to the invention is N-(4-chlorophenyl)-6-(isoquinolin-5-yl)pyridine-3-carboxamide (herein after referred to as V394)

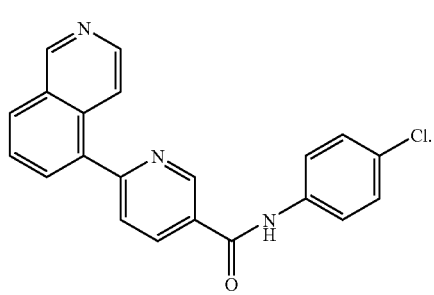

The compounds of formula (I) can be prepared by means of conventional methods, such as the reaction of a compound of formula (II)

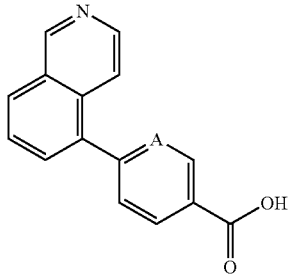

(II)

wherein A is as defined above and the carboxy group is activated as chloride
with a compound of formula (III)

Z—NH₂ (III)

wherein Z is as defined above.

Preferably, the compounds of formula (I) can be obtained by Suzuki reaction[2] between a compound of formula (IV)

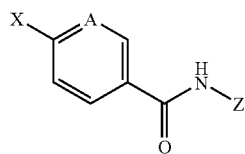

(IV)

wherein A and Z are as defined above and X is a halogen selected from iodine and bromine
and boronic acid (V)

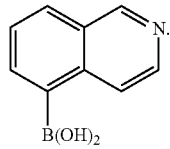

(V)

For example, compound V394 is conveniently prepared by Suzuki reaction between 6-bromo- or 6-chloro-N-(4-chlorophenyl)pyridine-3-carboxamide and isoquinolin-5-yl-5-boronic acid.

The compounds of formula (I) modulate the vanilloid TRPV1 receptor; the preferred compound V394 showed a $K_i$ value of 15 nM (13-17) in rat spinal chord and an $IC_{50}$ value of 0.83 nM (0.74-0.93) in cultured rat dorsal root ganglia neurons. Accordingly, the compounds of the invention can be used for the preparation of pharmaceutical compositions for the treatment of inflammatory states, such as chronic pain and inflammatory hyperalgesia. These formulations can be prepared by conventional methods and excipients, such as those disclosed in Remington's Pharmaceutical Science Handbook, XVII ed. Mack Pub., N.Y., U.S.A.

The invention will be herein after illustrated by means of the following example.

EXAMPLE

Materials and Methods

All commercially available compounds were purchased from Aldrich and were used without further purification. Reaction courses were monitored by thin-layer chromatography on silica gel (precoated $F_{254}$ Merck plates), the spots were examined with UV light and visualized with aqueous $KMnO_4$. Flash chromatography was performed using Merck silica gel (230-240 mesh). ¹H-NMR spectra were recorded on a Varian 400 MHz spectrometer using TMS as internal standard. Mass spectra were obtained with a Waters-Micromass ZMD spectrometer. Melting points were determined on a Buchi-Tottoli apparatus and are uncorrected.

EXAMPLE

N-(4-chlorophenyl)-6-(-isoquinolin-5-yl)pyridine-3-carboxamide (V394)

Step a)—6-Chloro-N-(4-chlorophenyl)pyridine-3-carboxamide

Commercially available 6-chloro-nicotinic chloride (56.8 mmol, 10 g) was dissolved in 50 ml of anhydrous $CH_2Cl_2$ and added dropwise to a solution of diisopropylethylamine (DIEA) (1.2 equivalents, 68.2 mmol, 11.67 ml) and 4-chloroaniline (1.2 equiv., 68.2 mmol, 8.70 g) in 50 ml $CH_2Cl_2$ at 0° C. The mixture was stirred at room temperature for 20 h, then diluted with $CH_2Cl_2$ (200 ml) and washed with water (1×200 ml) and brine (1×100 ml). The organic layer was dried over sodium sulphate and concentrated. The crude was crystallized from diethyl ether to give 13 g of a white solid. Yield=86%. ¹H NMR (CDCl₃, 200 MHz) δ 7.35 (2H, d, J=8.8 Hz), 7.47 (1H, d, J=8.2 Hz), 7.58 (2H, d, J=8.8 Hz), 7.88 (1H, bs), 8.16 (1H, dd, J=8.4 Hz, J'=2.8 Hz), 8.84 (1H, d, J=2.4 Hz)

Step b)—Isoquinolin-5-yl-5-boronic acid

A 2.5 M solution of n-BuLi (1.2 equiv., 3 mmol, 1.2 ml) in 20 ml of freshly distilled THF, cooled to −78° C., was added with a solution of 5-bromoisoquinoline (2.5 mmol, 520 mg) in 5 ml of THF. The resulting mixture was allowed to react at this temperature over 45'. A solution of triisopropylborate (1.2 equiv., 3 mmol, 0.7 ml) was then added and the mixture was stirred at the same temperature for 5' and then allowed to warm to room temperature and stirred for an additional hour. The mixture was quenched by slow addition of a 5% NaOH solution (30 ml). The aqueous layer was separated and acidified to pH 5/6 by addition of 10% HCl at 0° C. Extraction with ethyl acetate, evaporation of the organic phase and crystallisation from diethyl ether gave 250 mg of a white solid. Yield=58%. ¹H NMR (d₆-DMSO, 200 MHz) δ 7.66 (1H, t, J=7.2 Hz), 8.07 (1H, d, J=5.8 Hz), 8.13 (1H, d, J=8.0 Hz), 8.34 (1H, d), 8.47 (1H, d), 8.50 (2H, bs), 9.29 (1H, s); [M⁺¹] 174.1 ($C_9H_8BNO_2$ requires 172.98)

Step c)—N-(4-chlorophenyl)-6-(isoquinolin-5-yl) pyridine-3-carboxamide (Suzuki Reaction)

A mixture of isoquinolin-5-yl-5-boronic acid (1.5 equiv., 8.4 mmol, 1.46 g), 6-chloro-N-(4-chlorophenyl)pyridine-3-carboxamide (5.6 mmol, 1.5 g), palladium acetate (4% mol, 48 mg), triphenylphosphine (2 equiv., 2.94 g), 15% $Na_2CO_3$ (4 ml), EtOH (4 ml) and toluene (50 ml) was heated at 80° C. for 16 h. After evaporation, a saturated sodium bicarbonate solution was added and the precipitated solid was filtered and then washed with ethyl acetate. The residue was recrystallized from methanol to obtain 1.4 g of compound V394 as a white solid. M.p. (diethyl ether)=258° C. Yield=69%. $^1$H NMR (d$_6$-DMSO, 400 MHz) δ 7.471 (2H, d, J=8.8 Hz), 7.838 (1H, m), 7.852 (2H, d, J=8.8 Hz), 7.953 (1H, d, J=8.0 Hz), 8.049 (1H, dd, J=7.2 Hz, J'=0.8 Hz), 8.085 (1H, d, J=6.0 Hz), 8.290 (1H, d, J=8.4 Hz), 8.490 (1H, dd, J=8.4 Hz, J'=2.2 Hz), 8.543 (1H, d, J=6.0 Hz), 9.300 (1H, d, J=1.6 Hz), 9.438 (1H, s), 10.695 (1H, s); [M$^+$] 360.4 (C$_{21}$H$_{14}$ClN$_3$O requires 359.81).

Biological Assay

Newborn and adult Sprague-Dawley rats (~250 g) were used (Harlam, Italy). All experiments complied with the national guidelines and were approved by the regional ethics committee.

Radioligand Binding Assay

Male Sprague-Dawley rats with body weight between 250 to 350 g at the time for testing were used. For binding assays rats were sacrificed by decapitation under anesthesia and the spinal cord was removed and disrupted using a Polytron tissue homogenizer in ice cold buffer containing 5 mM KCl, 5.8 mM NaCl, 0.75 mM CaCl$_2$, 2 mM MgCl$_2$, 320 mM sucrose, 10 mM Hepes, pH 8.6.[5] The homogenized tissue was centrifuged at 1000×g for 10 min at 4° C. and the supernatant was centrifuged again at 35000×g for 30 min at 4° C. (Beckman Avanti J25). The pellet was resuspended in the same buffer as described above and used in binding experiments. In saturation experiments, 150 μg protein/sample from membrane suspensions were incubated with [$^3$H]-Resiniferatoxin ([$^3$H]-RTX) (0.003-3 nM) in the assay buffer containing 0.25 mg/ml fatty acid-free bovine serum albumin at 37° C. for 60 min. In competition experiments, the membranes were incubated at 37° C. for 60 min with [$^3$H]RTX (0.4 nM) and with increasing concentrations (from 0.1 nM to 3 μM) of examined compounds.

Non specific binding was evaluated in the presence of 1 μM RTX. After incubation the reaction mixture was cooled at 0° C. and incubated with bovine α1-acid glycoprotein (200 μg per tube) for 15 min to reduce non-specific RTX binding. Membrane-bound RTX was separated from free RTX by centrifuging the samples at 18500×g for 15 min. The tip of the microcentrifuge tube containing the pellet was cut off and the radioactivity was determined by scintillation counting (Packard 2500 TR). Protein concentration was determined according to a Bio-Rad method with bovine serum albumin as a standard reference (Bradford, 1976). Saturation and competition studies were analyzed with the Ligand program.[6]

Ca$^{2+}$ Fluorescence Measurements in Cultured Rat Dorsal Root Ganglia Neurones Adults rats were terminally anaesthetized and decapitated. Dorsal root ganglia were removed and placed in cold phosphate buffered solution (PBS) before being transferred to collagenase (10 mg/ml), trypsin (5 mg/ml) and DNAse (1 mg/ml) for 35 min at 37° C. The ganglia, placed in cold DMEM supplemented with 10% fetal bovine serum, 2 mM L-glutamine, 100 U/ml penicillin and 100 μg/ml streptomycin, were dissociated in single cells by several passages through a series of syringe needles (23 G down to 25 G). The medium and the ganglia were filtered to remove debris, topped up with 8 ml of DMEM medium and centrifuged (200×g for 5 min). The final cell pellet was re-suspended in DMEM medium [supplemented with 100 ng/ml mouse Nerve Growth Factor (mouse-NGF-7S) and cytosine-β-D-arabinofuranoside free base (ARA-C) 2.5 μM]. The cells were plated on poly-L-lysine (8.3 μM)- and laminin (5 μM)-coated 25 mm glass cover slips and kept for 5 to 8 days at 37° C. in a humidified incubator gassed with 5% CO$_2$ and air, then added with Fura-2-AM-ester (3 μM) in a Ca$^{2+}$ buffer solution having the following composition (mM): CaCl$_2$ 1.4, KCl 5.4, MgSO$_4$ 0.4, NaCl 135, D-glucose 5, HEPES 10 with BSA (0.1%), at pH 7.4, for 40 min at 37° C. The cells were then washed twice with the Ca$^{2+}$ buffer solution and transferred to a chamber on the stage of a Nikon eclipse TE300 microscope. Fura-2-AM-ester was excited at 340 nM and 380 nM to indicate relative [Ca$^{2+}$]$_i$ changes by the F$_{340}$/F$_{380}$ ratio recorded with a dynamic image analysis system (Laboratory Automation 2.0, RCS, Florence, Italy) and the cells were allowed (at least 10 min) to attain a stable fluorescence before beginning the experiment. A calibration curve was performed using buffer containing Fura-2-AM-ester and determinant concentrations of free Ca$^{2+}$. This curve was then used to convert the data obtained from the F$_{340}$/F$_{380}$ ratio to [Ca$^{2-}$]$_i$ (nM).[8] The effects of pretreatments with capsazepine (CPZ), SB366791 and V394 on the increase in [Ca$^{2+}$]$_i$ produced by 0.1 μM capsaicin were studied.

Capsaicin-Induced Secondary Allodynia in Rat

Capsaicin (20 nmols/50 μl/paw) was injected in the plantar surface of the glabrous skin of the right paw of rats anesthetized with diethyl ether (Chaplan et al., 1994). Compound V394 was orally administrated (30 μmol/kg) 2 hours prior to capsaicin injection. Tactile allodynia was evaluated 90 min after capsaicin challenge.

Drugs and Reagents

Drugs and reagents were obtained from the indicated companies: [$^3$H]-Resiniferatoxin (Perkin Elmer, Boston, Mass.), SB-366791 (Tocris, UK), capsaicin, capsazepine, ionomycin, laminin, poly-L-lysine, substance P (Sigma, Italy); mice NGF-7S and collagenase/dispase (Roche Diagnostics, Italy); Dulbecco's Modified Eagle's medium (DMEM), foetal bovine serum (FBS) heat inactivated, L-glutamine (200 mM), penicillin/streptomycin (10,000 IU/ml±10,000 UG/ml), (Gibco, Italy); Fura-2-AM-ester (Società Italiana Chimici, Italy). The stock concentrations of capsaicin (10 mM), capsazepine (10 mM), (E)-3-(4-chlorophenyl)-N-(3-methoxyphenyl)acrylamide (identified as SB-366791) (1 mM) and V394 were prepared in 50% DMSO and 50% Tween 80. Fura-2-AM-ester and ionomycin were dissolved in 100% DMSO. All other drugs were dissolved in distilled water. Appropriate dilutions were then prepared in Krebs buffer solution.

Results

Radioligand Binding Assay

The saturation curve of [$^3$H]-RTX to TRPV1 expressed in rat spinal cord showed a K$_D$ value of 0.21 (0.16-0.27) and a B$_{max}$ value of 57 (53-62) fmol/mg protein. The Scatchard plot was essentially linear and computer analysis of the data indicated that only one class of high affinity binding sites was present. Competition binding experiments of [$^3$H]-RTX revealed that V394 and the reference SB-366791 had a K$_i$ value of 15 (13-17) nM and 36 (30-43) nM respectively.

Ca$^{2+}$ Fluorescence

Capsaicin (0.1 μM) caused an increase in [Ca$^{2+}$] in the vast majority (95%) of dorsal root ganglia neurons, which were thereby identified as TRPV1 expressing neurons. The IC$_{50}$ value of V394 that inhibited capsaicin-evoked [Ca$^{2+}$]$_i$ mobilization was 0.83 nM (0.74-0.93). The reference TRPV1 antagonists, capsazepine and SB-366791, inhibited the capsaicin response with an $IC_{50}$ of 948 (676-1330) nM and 8.7 (3.4-17.3) nM, respectively. The results are expressed as mean and 95% fiducial limits.

Capsaicin-Induced Secondary Allodynia in Rat 90 min. after the capsaicin challenge, compound V394 produced a significant preventive effect (55%) against the pro-allodinic effect of capsaicin.

REFERENCES

1. Bakthavatchalam, R.; Blum, C. A.; Brielmann, H.; Darrow, J. W.; De Lombaert, S.; Yoon, T.; Zheugi, X. Neurogen Corporation WO 2004/056774, 170 pp.
2. Shieh, W. C.; Carlson, J. A. J. Org. Chem. 1992, 57, 379-381.
3. Zhang, J.; Assodi, J.; Charter, C.; L'hermite, N.; Weston, J. Tetrahedron Lett. 2001, 42, 6683-6686.
4. Meier, P.; Legraverant, S.; Mueller, S.; Schaub, J. Synthesis 2003, 4, 551-554.
5. a) Szallasi A. and Blunberg P. M. Neurosciences 1992, 8, 368. b) Szallasi A. and Blunberg P. M. Naunyn Schmiedeberg's Arch Pharmacol. 1993, 347, 84-91.
6. Munson, P. J.; Rodbard, D. Anal. Biochem. 1980, 107, 220-239.
7. Rigoni, M.; Trevisani, M.; Gazzieri, D.; Nadaletto, R.; Tognetto, M.; Creminon, C.; Davis, J. B.; Campi, B.; Amatesi, S.; Geppetti, P.; Harrison, S. Br. J. Pharmacol. 2003, 138, 977-985.
8. Kudo, Y.; Ozaki, K.; Miyakawa, A.; Amano, T.; Ogura, A. Jap. J. Pharmacol. 1986, 41, 345-351.

The invention claimed is:

1. A compound of formula (I)

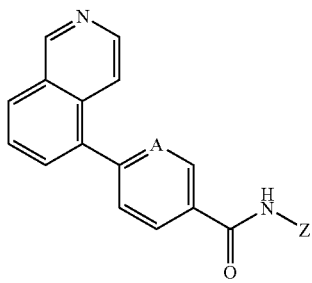

(I)

wherein:

A is CH or N; and

Z is a phenyl or a pyridyl ring.

2. The compound according to claim 1, wherein Z is substituted with one or two R groups, which can be the same or different from one another and R is selected from methyl, isopropyl, tert-butyl or trifluomethyl.

3. The compound according to claim 1, wherein the compound has formula (Ia)

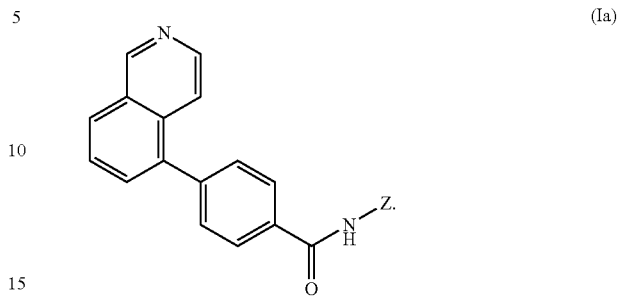

(Ia)

4. The compound according to claim 1, wherein the compound has formula (Ib)

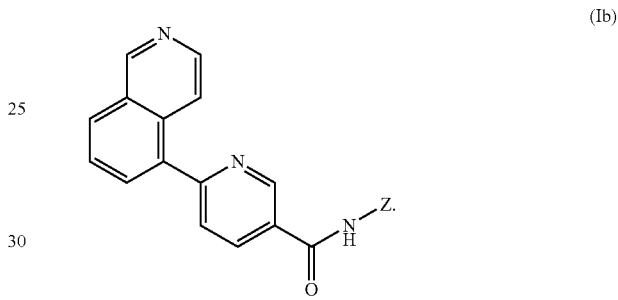

(Ib)

5. The compound according to claim 4, wherein the compound has formula:

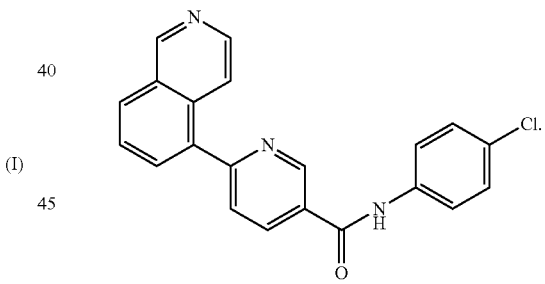

6. The compound of claim 1, wherein Z is substituted with one or two R groups, which can be the same or different from one another and are selected from $C_1$-$C_4$ alkyl, $C_1$-$C_4$ haloalkyl, or halogen.

7. The compound of claim 3, wherein Z is substituted with one or two R groups, which can be the same or different from one another and are selected from $C_1$-$C_4$ alkyl, $C_1$-$C_4$ haloalkyl, or halogen.

8. The compound of claim 4, wherein Z is substituted with one or two R groups, which can be the same or different from one another and are selected from $C_1$-$C_4$ alkyl, $C_1$-$C_4$ haloalkyl, or halogen.

9. A medicament comprising the compound according to claim 1.

10. The medicament of claim 9, wherein Z is substituted with one or two R groups, which can be the same or different from one another and are selected from $C_1$-$C_4$ alkyl, $C_1$-$C_4$ haloalkyl, or halogen.

11. A pharmaceutical composition containing a compound of claim 1 in admixture with pharmaceutically acceptable carriers and/or excipients.

12. The pharmaceutical composition of claim 11, wherein Z is substituted with one or two R groups, which can be the same or different from one another and are selected from $C_1$-$C_4$ alkyl, $C_1$-$C_4$ haloalkyl, or halogen.

13. The pharmaceutical composition of claim 12, wherein R is selected from methyl, isopropyl, tert-butyl or trifluomethyl.

14. The pharmaceutical composition of claim 11, wherein the compound has formula (Ia)

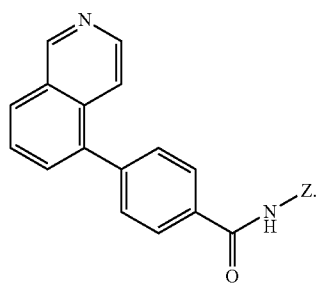

(Ia)

15. The pharmaceutical composition of claim 14, wherein Z is substituted with one or two R groups, which can be the same or different from one another and are selected from $C_1$-$C_4$ alkyl, $C_1$-$C_4$ haloalkyl, or halogen.

16. The pharmaceutical composition of claim 11, wherein the compound has formula (Ib)

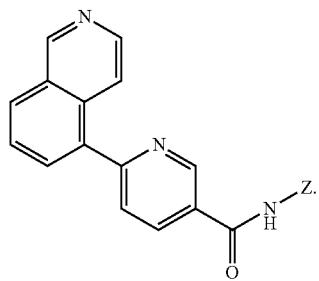

(Ib)

17. The pharmaceutical composition of claim 16, wherein Z is substituted with one or two R groups, which can be the same or different from one another and are selected from $C_1$-$C_4$ alkyl, $C_1$-$C_4$ haloalkyl, or halogen.

18. The pharmaceutical composition of claim 11, wherein the compound has formula:

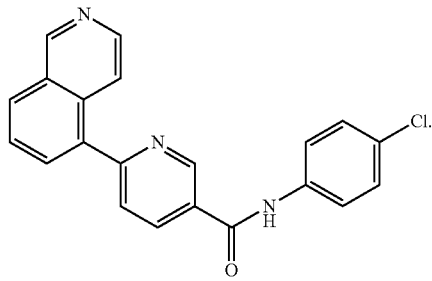

19. A method for preparation of medicaments for the treatment of an inflammatory disease and/or a urological disorder, the method comprising admixing the compound of claim 1 with a pharmaceutically acceptable carriers and/or excipients.

20. The method of claim 19, wherein the inflammatory disease is neuropathic pain.

21. A method for treating an inflammatory disease and/or a neurological disorder, the method comprising
administering to an individual a therapeutically effective amount of the compound of claim 1.

22. The method of claim 21, wherein Z is substituted with one or two R groups, which can be the same or different from one another and are selected from $C_1$-$C_4$ alkyl, $C_1$-$C_4$ haloalkyl, or halogen.

23. The method of claim 21, wherein the compound has formula (Ia)

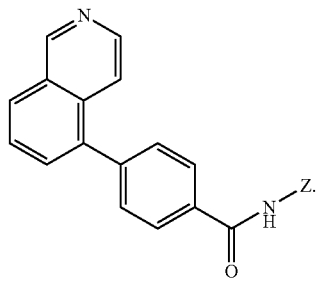

(Ia)

24. The method of claim 23, wherein Z is substituted with one or two R groups, which can be the same or different from one another and are selected from $C_1$-$C_4$ alkyl, $C_1$-$C_4$ haloalkyl, or halogen.

25. The method of claim 21, wherein the compound has formula (Ib)
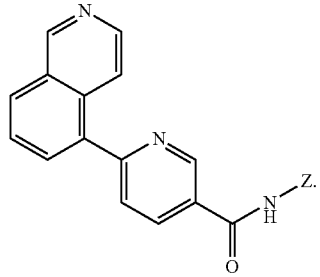
(Ib)
26. The method of claim 25, wherein Z is substituted with one or two R groups, which can be the same or different from one another and are selected from $C_1$-$C_4$ alkyl, $C_1$-$C_4$ haloalkyl, or halogen.
27. The method of claim 21, wherein the compound has formula:
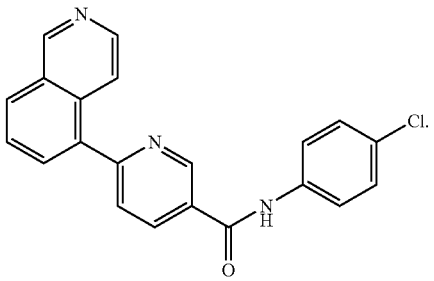
* * * * *